(12) United States Patent
Brossard et al.

(10) Patent No.: US 11,931,436 B2
(45) Date of Patent: Mar. 19, 2024

(54) WATER-IN-OIL EMULSION FOR SKIN OR LIP CARE OR MAKEUP

(71) Applicant: LVMH RECHERCHE, Saint Jean de Braye (FR)

(72) Inventors: Fabienne Brossard, Orleans (FR); Valérie De La Poterie, Lailly en Val (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/616,895

(22) PCT Filed: Dec. 13, 2018

(86) PCT No.: PCT/FR2018/053267
§ 371 (c)(1),
(2) Date: Nov. 25, 2019

(87) PCT Pub. No.: WO2019/115958
PCT Pub. Date: Jun. 20, 2019

(65) Prior Publication Data
US 2021/0169751 A1    Jun. 10, 2021

(30) Foreign Application Priority Data
Dec. 14, 2017   (FR) ...................................... 1762186

(51) Int. Cl.
*A61K 8/06* (2006.01)
*A61K 8/42* (2006.01)
*A61K 8/81* (2006.01)
*A61K 8/92* (2006.01)
*A61Q 1/06* (2006.01)

(52) U.S. Cl.
CPC ................ *A61K 8/064* (2013.01); *A61K 8/42* (2013.01); *A61K 8/8152* (2013.01); *A61K 8/8182* (2013.01); *A61K 8/92* (2013.01); *A61Q 1/06* (2013.01)

(58) Field of Classification Search
None
See application file for complete search history.

(56) References Cited

U.S. PATENT DOCUMENTS

| | | |
|---|---|---|
| 7,244,419 B2 | 7/2007 | Yamato et al. |
| 10,045,922 B1 | 8/2018 | Kanemoto |
| 10,045,930 B2 * | 8/2018 | Viala ........................ A61K 8/87 |
| 2012/0164093 A1 | 6/2012 | Do et al. |

FOREIGN PATENT DOCUMENTS

| | | |
|---|---|---|
| CN | 106170319 A | 11/2016 |
| FR | 2820739 | 8/2002 |
| JP | 2018203625 A | 12/2018 |
| WO | 2015154928 A1 | 10/2015 |
| WO | 2016039771 | 3/2016 |
| WO | WO 2016039771 * | 3/2016 |

OTHER PUBLICATIONS

CSR TKBTrading "Cosmetic Ingredient Octyldodecanol for Lip Products and Skincare". https://tkbtrading.com/blogs/whats-new-at-tkb-trading/cosmetic-ingredient-octyldodecanol 2021.*
Mintel Sheet No. 4601375, Make-Up Art Cosmetics, M.A.C. Chinese New Year 2017: "Matte Lipstick," Date Published: Feb. 2017, (3 pages).
International Search Report and Written Opinion issued for International Patent Application No. PCT/FR2018/053267, dated Feb. 18, 2019, 12 pages including English translation of Search Report.

* cited by examiner

*Primary Examiner* — Danah Al-Awadi
(74) *Attorney, Agent, or Firm* — Hamre, Schumann, Mueller & Larson, P.C.

(57) ABSTRACT

The invention relates to a wax-free water-in-oil emulsion comprising an amide of amino acid and of fatty acid, and a polymer bearing alkyl chains comprising 10 to 30 carbon atoms. This emulsion is intended for skin or lip care or makeup.

9 Claims, 1 Drawing Sheet

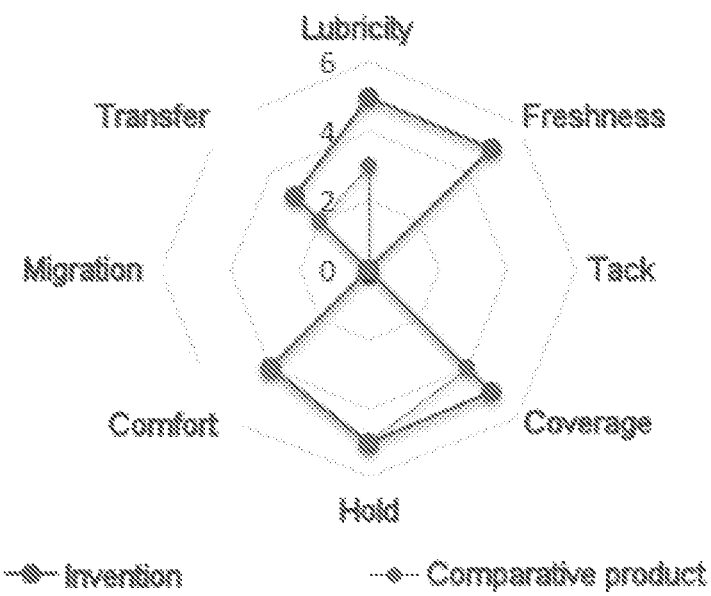

WATER-IN-OIL EMULSION FOR SKIN OR LIP CARE OR MAKEUP

The present invention relates to a water-in-oil emulsion comprising an amide of amino acid and long-chain fatty acid, and a polymer bearing alkyl chains comprising 10 to 30 carbon atoms. This emulsion is intended for skin or lip care or makeup.

PRIOR ART

The invention pertains to new water-in-oil emulsions which are equipped with hues, sensorial qualities, and durability that have never been obtained simultaneously, having to date been incompatible.

For example, in order to obtain a natural effect also called "nude", emulsions are formulated so that a small amount of material is applied to the part of the body that is desired (skin or lips, for example). Generally, though, the less the amount of material applied, the lower the resistance of the resulting film to friction, to perspiration, or to movements in the skin, and the lower the intensity of the colors. On the other hand, if the aim is to improve the hold or adhesion of the film, the risk is run of decreasing its flexibility and softness, since generally a greater amount of material is applied.

There are numerous lip or skin makeup or care products that are based on oils. These may be anhydrous or emulsion products.

Some of these products, when they contain neither wax nor water, have an attractive appearance such as transparency or beauty of the hues. However, they provide no sensation at all of freshness on application, and, once applied, they lack coverage.

Moreover, products which contain waxes in order to provide coverage exhibit the drawbacks linked to the crystallinity of the waxes. The hues are dull and not very attractive; the makeup effect is matte; the applied product left on the skin or lips leaves the sensation of a waxy, uncomfortable, heavy, and present film; and the products attach at the moment of their application, which consequently lacks lubricity.

There is a need, therefore, to combine the advantages of an anhydrous product with the freshness and sensorial qualities of an emulsion, without the drawbacks caused by waxes, which are needed in the prior art in order to obtain a product in paste or stick form that provides sufficient coverage of the skin and lips.

There is also a need to have a composition which when applied to the skin or lips gives low thickness and good durability. When the composition contains pigments, the effect of the color can be intense in spite of the small amount of material applied to the skin or lips.

A desire more specifically is to give greater consistency to a product containing oils, but without using waxes as a structuring means, with the product also containing water in order to provide freshness. The aim is to replace the waxes which reduce the lubricity of the product on application, which form an uncomfortable film on the skin or lips, and which dull the hues.

GENERAL DESCRIPTION OF THE INVENTION

The invention therefore relates to a composition in emulsion form which has been made solid or pastelike not by a crystalline network of waxes but instead by the mixture of an amide of glutamic acid or of aspartic acid and a hydrocarbon polymer, where said mixture may be solubilized by at least one nonvolatile oil. Very surprisingly, this composition unites sensorial qualities with performance.

DETAILED DESCRIPTION

According to one embodiment, the invention pertains to a cosmetic skin or lip care or makeup composition in the form of a water-in-oil emulsion comprising a fatty phase, a surfactant, and water, characterized in that said fatty phase comprises at least one amide of glutamic acid or of aspartic acid, said amide comprising at least one alkoyl group having 6 to 14 carbon atoms, and comprises at least one alkyl vinyl (co)polymer comprising at least one alkyl substituent comprising 10 to 30 carbon atoms.

The composition preferably comprises an amount of wax(es) of less than 5% by mass, and more preferably less than 3% by mass, or even less than 2% by mass. The composition preferably contains less than 1% by mass of wax(es), and more preferably still is devoid of wax(es).

The composition of the invention does not exhibit the disadvantages mentioned above with regard to the anhydrous products and/or wax-comprising products, especially those in the form of pastes or sticks or those which are cast in cups.

Following application to the skin or lips, this composition is able advantageously to form an applied product of low thickness with a cosmetic effect which persists over time. When the composition includes pigments, the effect of the color can be intense in spite of the small amount of material applied to the skin or lips.

In one more particular embodiment, the invention pertains to a care or makeup composition with a consistency which may be solid or creamy, in the form of a water-in-oil emulsion comprising a fatty phase, a surfactant, and water, said fatty phase itself comprising at least one first, hydrocarbon nonvolatile oil and at least one second nonvolatile oil comprising at least one ester or alcohol function, these oils being miscible, said composition further comprising an alkyl polymer comprising at least one alkyl substituent comprising 10 to 30 carbon atoms, and at least one alkyl amide of glutamic acid or of aspartic acid in an amount sufficient to provide the solid, structured or creamy character of the composition.

By virtue of this combination of ingredients, a product is obtainable which is very easy and quick to apply to the skin or lips and which in its applied form is surprising for its extreme lubricity, and which forms a light, comfortable, intensely colored film which is long-lasting on the skin or lips. By virtue of the invention, a very good hold is obtained at the same time as a film which is light and flexible and therefore very comfortable. To date it was impossible to bring together all of these properties in the formulation of products structured using waxes, and they were never obtained simultaneously in the prior art. In particular, the performance characteristics of long durability of a film applied to the skin or lips are obtained in the prior art, but using films which are present and uncomfortable because they contain waxes.

The sensorial qualities of the composition according to the invention are highly surprising to the consumer, since the composition is very lubricious, easy to apply in a single pass, and provides freshness, hold, comfort owing to the fineness of the applied film, and an intense color.

The continuous phase of the emulsion of the invention is a fatty phase in which at least one of the oils present is structured by an amide of glutamic acid (glutamide) or by an amide of aspartic acid. These amides, consequently, are structuring agents for said oil, which may be selected from hydrocarbon oils, ester oils, and alcohol oils.

The amide preferably comprises at least one alkoyl group comprising 6 to 14 carbon atoms, such as 8 or 12 carbon atoms, for example. An amide of glutamic acid of this kind is described for example in patent FR 2 820 739.

The glutamide is preferably selected from dibutyl lauroyl glutamide, dibutyl ethylhexanoyl glutamide, and mixtures thereof, and may for example be one of the branded products EB-21, GP-1, AJK-OD2046, AJK-BG2055, and AJK-CE2046 manufactured by Ajinomoto.

The amide of glutamic acid is for example selected from dibutyl lauroyl glutamide and dibutyl ethylhexanoyl glutamide. According to one embodiment, the composition comprises dibutyl lauroyl glutamide and dibutyl ethylhexanoyl glutamide.

The amide or mixture of amides, especially of glutamide(s), represents, for example, between 0.1% and 15.0% by mass, between 1.0% and 15.0% by mass, between 0.5% and 8.0% by mass, between 1.0% and 5.0% by mass, between 0.8% and 5% by mass, or even between 2.0 and 3.0% by mass relative to the mass of the composition.

The composition of the invention comprises at least one alkyl vinyl (co)polymer. This (co)polymer is preferably noncrosslinked and solubilized in one of the oils of the fatty phase.

It may be obtained by polymerization of a monomer comprising at least one alkyl group having 10 to 30 carbon atoms, said monomer being selected from an alkyl(meth)acrylic acid or ester thereof; an alkyl (meth)acrylate; and an alkylpyrrolidone.

It may also be obtained by polymerization of a mixture of vinylpyrrolidone and an alpha-olefin comprising 14 to 22 carbon atoms, preferably 16 to 20 carbon atoms.

According to one embodiment, the alkyl vinyl (co)polymer is obtained from an alkyl (meth)acrylate monomer in which the alkyl group comprises 10 to 30 carbon atoms, for example 14, 16, 18, 20 or 22 carbon atoms.

In another embodiment, the alkyl vinyl (co)polymer originates from the polymerization of a first, stearyl (meth)acrylate or behenyl (meth)acrylate monomer, this monomer being grafted with a silicone group such as, for example, polydimethylsiloxane, and optionally of at least one second monomer selected from (meth)acrylic acid, methyl methacrylate, butyl methacrylate, and 2-ethylhexyl acrylate. The compounds in question may for example be those with INCI name Acrylates/Behenyl Acrylate/Dimethicone Methacrylate Copolymer or the INCI name Acrylates/Stearyl Acrylate/Dimethicone Methacrylate Copolymer, and may be commercial products with names KP-561P or KP-562P, which are sold by Shin Etsu.

The alkylpyrrolidone in which the alkyl group comprises 10 to 30 carbon atoms preferably has an alkyl group comprising 30 carbon atoms (INCI name Triacontanyl PVP).

The alkyl vinyl (co)polymer may also originate from the polymerization of a mixture of vinylpyrrolidone with an alpha-olefin comprising 14 to 22 carbon atoms, preferably comprising 16 to 20 carbon atoms, and, for example, 1-eicosene (INCI name VP/Eicosene Copolymer) or 1-hexadecene (INCI name VP/Hexadecene Copolymer). Products of these kinds are sold under the brand names Antaron® or Unimer®.

Lastly, the alkyl vinyl (co)polymer may be a homopolymer of an alkyl (meth)acrylate in which the alkyl group comprises 10 to 30 carbon atoms, such as the products with brand name Intelimer®, or with INCI name C10-C30 Alkyl Acrylate.

The alkyl vinyl (co)polymer may represent between 1% and 30% by mass of the mass of the composition, according to the intended use. The (co)polymer thus represents, for example, between 15% and 25% by mass for a lipstick, between 5 and 10% by mass for an eye liner, and between 1 and 5% by mass for a foundation.

The vinyl (co)polymer may be selected from the compounds bearing the INCI names Acrylates/Dimethicone Methacrylate Copolymer, Acrylates/Behenyl Acrylate/Dimethicone Methacrylate Copolymer, Acrylates/Stearyl Acrylate/Dimethicone Methacrylate Copolymer, C10-C30 Alkyl Acrylate, VP/Eicosene Copolymer, VP/Hexadecene Copolymer or Triacontanyl PVP.

In some embodiments, the composition contains from 1 to 15% by mass of Triacontanyl PVP, from 15 to 25% by mass of an Acrylates/Stearyl Acrylate/Dimethicone Methacrylate, or from 15 to 25% by mass of a mixture of VP/Eicosene and an Acrylates/Stearyl Acrylate/Dimethicone Methacrylate.

The composition may comprise any type of volatile or nonvolatile oil known to the skilled person, such as a silicone oil, a hydrocarbon oil or an oil comprising carbon, hydrogen, and oxygen.

The fatty phase may comprise at least one first, hydrocarbon nonvolatile oil and at least one second nonvolatile oil comprising at least one ester function and/or at least one alcohol function, and at least one hydrocarbon chain comprising 10 to 22 carbon atoms, referred to hereinafter as "alcohol or ester oil".

According to one embodiment, preference is given to using a small amount of silicone oils (oil comprising at least one silicon atom), which are sometimes detrimental to the stability of the composition and to good preservation thereof. In one preferred embodiment, the composition contains less than 3% by mass, preferably less than 1% by mass, of a silicone oil. It is preferably devoid of such an oil.

Among the ester or alcohol oils, preference is given to oils composed of carbon, oxygen, and hydrogen atoms and comprising at least one hydrocarbon chain comprising 10 to 22 carbon atoms and being linear or branched, saturated or unsaturated; for example, oils selected from isostearyl isostearate, liquid, saturated linear or branched alcohols such as octyldodecanol, dimer esters of dilinoleic acid (such as the product with INCI name Dimer Dilinoleyl Dimer Dilinoleate, of which a commercial representative is Lusplan® DD DA7), pentaerythrityl triisostearate, trimethylolpropane triisostearate, and 2-octyldodecyl 12-stearoyl stearate (for example, the oil with a commercial name of Ceraphyl® 847).

Among the hydrocarbon oils, preference will be given to oils selected from polybutenes, hydrogenated polyisobutenes, hydrogenated polydecenes, the mineral oil also called liquid paraffin (with INCI names of Mineral Oil or Paraffinum Liquidum, an example being the mineral oil with brand name Primol® 352). A hydrocarbon oil is defined in accordance with the general knowledge of the skilled person and may be an oil composed of carbon and hydrogen, of alkane or alkene type.

The ester or alcohol oil, when present in the composition, is preferably miscible with the hydrocarbon oil in such a way that the fatty phase is optimally structured by the amide, preferably glutamide.

The ratio by mass between the first nonvolatile oil and the second nonvolatile oil is preferably between 1/3 and 3/1, preferably between 1/1 and 3/1.

Further to the aforementioned oils, the composition may comprise at least one volatile oil, which may be selected from isododecane, isohexadecane, alkane cocoates (for example, the products with tradename Vegelights®), and cyclopentasiloxane. The amount of volatile oil(s) may be between 5 and 15% by mass.

The composition may comprise from 8 to 40% by mass of a first hydrocarbon nonvolatile oil, from 8 to 12% by mass of a volatile oil, and from 8 to 40% by mass of a second oil which is an ester or alcohol oil.

According to one embodiment, the composition comprises from 15 to 40% by mass of a first, hydrocarbon nonvolatile oil, from 8 to 12% by mass of a volatile oil, and from 8 to 15% by mass of a second, ester or alcohol nonvolatile oil.

According to another embodiment, the composition comprises from 8 to 15% by mass of a first, hydrocarbon nonvolatile oil, from 8 to 12% by mass of a volatile oil, and from 15 to 40% by mass of a second, ester or alcohol nonvolatile oil.

The composition of the invention may be used for skin or lip care or makeup.

The composition of the invention may be used for manufacturing makeup products for the lips or for the skin (foundation, eyeshadow or rouge, UV-protective care products and perfecting care products).

The composition may take on a variety of forms, such as a serum, a lotion, a cream or a hydrogel, a mask, a stick or a patch. According to one form of implementation, the composition is solid.

According to one embodiment, the composition is solid in the sense in which it is understood by a skilled person. In some embodiments, it is not necessary to place the composition into a container for it to be preserved. It may, nevertheless, require an applicator.

A composition which is not solid is, for example, a flask, heating-pack or bottle product such as a mascara applied with a brush, a gloss applied with a foam tip, a foundation in flask, a care lotion or a care cream, these examples having no limiting effect.

The composition of the invention may be obtained by mixing the nonvolatile ingredients of the fatty phase at a temperature sufficient to cause the phase to melt, by introducing the preheated aqueous phase into the melted fatty phase, by adding the pigmentary phase containing pigments and also fillers, and then by adding, where appropriate, a volatile oil, to give a fluid mixture.

According to one embodiment, the composition is in solid form. In this case it may be cast and/or molded, i.e., obtained by a method comprising a step of preparing the above-described fluid mixture, a step of casting the fluid mixture into a container, a step of cooling (cast composition), and optionally a step of demolding (cast and molded composition). The container may be a low-thickness cup or a cylindrical mold.

According to another embodiment, the composition is in the form of a paste, also called a destructured form. In that case, the fluid mixture is cooled to ambient temperature with stirring.

The present invention therefore provides a method for manufacturing a composition as described above, which comprises at least the following steps:
- the water and the surfactant are mixed and heated to give an aqueous phase,
- the fatty phase comprising the amide and the alkyl vinyl (co)polymer is melted,
- the aqueous phase is introduced into the melted fatty phase, to give a fluid mixture, and
- the fluid mixture is left to cool to ambient temperature, to give a composition in solid or creamy form.

According to a first variant, the fluid mixture is poured into a mold and then left to cool, after which it is demolded, to give the composition of the invention in solid form.

According to a second variant, the fluid mixture is left to cool to ambient temperature with continuous stirring, to give the composition of the invention in the form of a paste, which can subsequently be poured into packaging.

The composition may take the form of a stick such as a lipstick, a lip balm, a corrective stick, a foundation, a rouge or an eyeshadow.

The stick is preferably in the form of a cylinder, which may have a standard diameter of 11.8 mm, 12.1 mm, 12.7 mm, 9.5 mm or 11.6 mm.

In the water-in-oil emulsion of the invention, the water represents preferably between 10% and 35% by mass of the mass of the composition.

The composition may comprise film-forming polymers which are dispersed in water or solubilized in water. According to one embodiment, the compositions are devoid of such polymers.

The composition may also include other ingredients, which participate in the stability and also in the hold of the product, such as fatty substances with a pastelike consistency at 25° C., and fillers such as silica, PMMA, fluorophlogopites or nylon.

The composition may further comprise at least one cosmetically acceptable excipient selected from pigments, active agents, dyes, additional polymers, additional rheological agents, perfumes, electrolytes, pH modifiers, antioxidants, preservatives, moisturizers, humectants, organic or inorganic sunscreen agents, or nacres.

The compounds in particulate form (powders) such as the pigments and the fillers represent preferably between 10% and 30% by mass of the mass of the composition, according to the hue it is desired to obtain.

The surfactant is preferably a surfactant capable of stabilizing water-in-oil emulsions, selected from compounds having the INCI name PEG-30 Dipolyhydroxystearate (for example the brand name Cithrol® DPHS-SO), Disteardimonium Hectorite and Polyglyceryl-6 Polyricinoleate and Polyglyceryl-2 Isostearate (for example the brand name Nikkomulese® WO-NS), and Sorbitan Sesquioleate (for example the brand name Span® 83). The surfactant represents in particular between 0.5% and 5% by mass of the mass of the composition.

The invention also describes a cosmetic skin or lip care or makeup method which comprises applying a composition as described above.

DESCRIPTION OF THE FIGURE

FIG. 1 presents the result of an evaluation of the sensorial properties of the lipstick according to the invention from Example 2.

The invention is illustrated by the examples which follow.

EXAMPLE 1: COMPOSITIONS OF THE INVENTION

The composition of products according to the invention is described in the tables hereinafter. The percentages given are by mass.

Lipstick

| Phase | INCI name | % |
| --- | --- | --- |
| A | DIBUTYL LAUROYL GLUTAMIDE | 1.3 |
| A | DIBUTYL ETHYLHEXANOYL GLUTAMIDE | 0.9 |
| A | OCTYLDODECANOL | 8.8 |
| A | HYDROGENATED POLYISOBUTENE | 16.7 |

-continued

| Phase | INCI name | % |
|---|---|---|
| A | VP/EICOSENE COPOLYMER | 10.0 |
| A | ACRYLATES/STEARYL ACRYLATE/ DIMETHICONE METHACRYLATE COPOLYMER | 10.0 |
| A | PEG-30 DIPOLYHYDROXYSTEARATE | 3.5 |
| B | AQUA | qs 100 |
| B | Preservatives | 2.9 |
| C | PIGMENTS | 10.0 |
| D | SILICA | 5.0 |
| D | SILICON DIOXIDE | 5.0 |
| E | ISODODECANE | 10.0 |

Preparation Process

Phase A is heated to 90-95° C. on a water bath with stirring and is homogenized until melting is complete.
Phase B is heated to 85° C. on a water bath and with stirring.
Phase B is poured into phase A and the mixture is homogenized for several minutes with stirring.
The pigmentary phase C and then the various fillers D are added in succession.
Phase E is added.
The resulting composition is cast directly at between 85° C. and 90° C. into a lipstick mechanism with an internal diameter of between 9 and 12 mm.
The composition is left in the mechanism to return to ambient temperature.
The composition is demolded when solid after approximately 1 h.

Foundation

| Phase | INCI name | % |
|---|---|---|
| A | DIBUTYL LAUROYL GLUTAMIDE | 1.7 |
| A | DIBUTYL ETHYLHEXANOYL GLUTAMIDE | 1.1 |
| A | OCTYLDODECANOL | 11.0 |
| A | HYDROGENATED POLYDECENE | 19.0 |
| A | ETHYLHEXYL METHOXYCINNAMATE | 5.5 |
| A | DIETHYLAMINO HYDROXYBENZOYL HEXYL BENZOATE | 1.1 |
| A | BIS-ETHYLHEXYLOXYPHENOL METHOXYPHENYL TRIAZINE | 1.1 |
| A | TRIACONTANYL PVP | 3.2 |
| A | PEG-30 DIPOLYHYDROXYSTEARATE | 3.7 |
| B | AQUA | qs 100 |
| B | PROPANEDIOL | 5.2 |
| B | Preservatives | 3.0 |
| C | PIGMENTS | 11.0 |
| D | ISODODECANE | 10.5 |
| E | TITANIUM DIOXIDE | 4.0 |

Preparation Process

Phases A to C are prepared and mixed by the same process as that used to manufacture the lipstick above, phases D and E are added at the end, and then the resulting composition is cast while hot into cups and then left to cool to ambient temperature, or left to cool with stirring to ambient temperature, to give a paste.

Eye liner

| Phase | INCI name | % by mass |
|---|---|---|
| A | DIBUTYL LAUROYL GLUTAMIDE | 1.3 |
| A | DIBUTYL ETHYLHEXANOYL GLUTAMIDE | 0.8 |
| A | OCTYLDODECANOL | 8.8 |
| A | HYDROGENATED POLYISOBUTENE | 16.9 |
| A | ISOSTEARYL ISOSTEARATE | 5.0 |
| A | TRIACONTANYL PVP | 10.0 |
| A | PEG-30 DIPOLYHYDROXYSTEARATE | 3.5 |
| B | AQUA | qs 100 |
| B | PROPANEDIOL | 5.0 |
| B | Preservatives | 2.9 |
| C | CI 77499 (IRON OXIDE) | 9.7 |
| D | SILICA | 3.0 |
| E | ISODODECANE | 10.0 |

Preparation Process

Phases A to E are prepared and mixed by the same process as used to manufacture the lipstick of example 1, the only difference being that the final mixture obtained is cast while hot directly into pen mechanisms with a diameter of between 1 and 5 mm.

EXAMPLE 2: PRIOR-ART LIPSTICK CONTAINING WAXES, AND LIPSTICK OF THE INVENTION

Lipstick According to the Invention

The composition is a water-in-oil emulsion with a formula as follows (% expressed by mass):

| Phase | INCI name | % |
|---|---|---|
| A | DIBUTYL ETHYLHEXANOYL GLUTAMIDE | 0.8 |
| A | DIBUTYL LAUROYL GLUTAMIDE | 1.3 |
| A | OCTYLDODECANOL | 8.8 |
| A | HYDROGENATED POLYDECENE | 16.6 |
| A | PEG-30 DIPOLYHYDROXYSTEARATE | 3.5 |
| A | ACRYLATES/STEARYL ACRYLATE/ DIMETHICONE METHACRYLATE COPOLYMER | 20.0 |
| B | AQUA | qs 100 |
| B | Preservatives | 2.9 |
| C | PIGMENTS | 9.9 |
| D | SILICON DIOXIDE | 10.0 |
| E | ISODODECANE | 10.0 |

The composition is molded to sticks by the process described in example 1.

Comparative Lipstick

The comparative composition has a formula as follows (% expressed by mass):

| Phase | INCI name | % |
|---|---|---|
| A | POLYGLYCERYL-2 TRIISOSTEARATE | 23.3 |
| A | TRIMETHYLOLPROPANE TRIISOSTEARATE | 11.0 |
| A | JOJOBA ESTERS | 10.1 |
| A | POLYETHYLENE | 9.5 |
| A | CERA MICROCRISTALLINA | 8.3 |
| A | ACRYLATES/STEARYL ACRYLATE/ DIMETHICONE METHACRYLATE COPOLYMER | 5.0 |
| A | HYDROGENATED POLYISOBUTENE | 2.5 |
| B | PIGMENTS | 11.3 |
| C | ISODODECANE | 19.0 |
| | TOTAL | 100.00 |

Evaluation of Hold Properties

Evaluation Protocol:

The hold of the lipstick of the invention and of the comparative lipstick were compared. A measurement was made of the thickness of the film in vivo over a total time of 6 hours. Each measurement corresponds to the mean of three measurements performed on three sticks identical in composition.

Panel of ten people (women aged 20 to 50)

The film thickness measurements are performed at T0, T4H and T6H for each of the two products. Calculations are then made of the percentage (T0-T4H)/T0 and the percentage (T0-T6H)/T0.

Results:

The results are presented in table 1 below.

TABLE 1

Measurement of lipstick hold

| Time | Reduction in film thickness | |
|---|---|---|
| | Invention | Comparative |
| T + 4 h | −1% | 0% |
| T + 6 h after lunch | −6% | −11% |

The thickness of the residual film on the lips of the composition according to the invention is significantly greater than for the comparative composition containing waxes.

Evaluation of Sensorial Properties

Evaluation Protocol:

Eight sensorial descriptors are used to describe the feeling of the composition on the lips at application Panel of ten people (women aged 20 to 50)

Scale: ratings from 0 to 6=>0=highly mediocre/6=excellent

Results:

The results are presented in table 2 below and in FIG. 1.

TABLE 2

Sensorial properties of lipsticks

| Property | Invention | Comparative |
|---|---|---|
| Lubricity | 5 | 3 |
| Freshness | 5 | 0 |
| Tack | 0 | 0 |
| Coverage | 5 | 4 |
| Hold | 5 | 5 |
| Comfort | 4 | 4 |
| Migration | 0 | 0 |
| Transfer | 3 | 2 |

The composition according to the invention is significantly fresher and more lubricious than the comparative composition containing waxes.

EXAMPLE 3: LIPSTICK ACCORDING TO THE INVENTION

The composition according to the invention is prepared with the following ingredients (% expressed by mass).

| Phase | INCI name | % |
|---|---|---|
| A | DIBUTYL LAUROYL GLUTAMIDE | 1.56 |
| A | DIBUTYL ETHYLHEXANOYL GLUTAMIDE | 1.0 |
| A | OCTYLDODECANOL | 10.4 |
| A | HYDROGENATED POLYDECENE | 33.0 |
| A | TRICONTANYL PVP COPOLYMER | 5.0 |
| A | BIS-BEHENYL/ISOSTEARYL/PHYTOSTERYL DIMER DILINOLEYL DIMER DILINOLEATE | 1.0 |
| A | PEG-30 DIPOLYHYDROXYSTEARATE | 3.5 |
| B | AQUA | qs 100 |
| B | Preservatives | 2.9 |
| C | PIGMENTS | 10.0 |

-continued

| Phase | INCI name | % |
|---|---|---|
| D | SILICA | 2.5 |
| D | METHYL METHACRYLATE CROSSPOLYMER | 2.5 |
| E | ISODODECANE | 10.0 |

Preparation Process

The preparation process is the same as that described in example 1.

Evaluation of Sensorial Properties

The sensorial properties of the lipstick of the invention and of a lipstick in the form of an anhydrous stick containing waxes (product from Mintel sheet No. 4601375) were evaluated by a panel of experts trained in the sensorial analysis of lipsticks. The texture, the immediate efficacy, and the makeup outcome were rated more particularly.

Evaluation Protocol:

The study was carried out on a panel of 17 women (of 20 to 50 years in age) who attended a sensorial analysis room on a weekly basis. The evaluation conditions were standardized through use of descriptors relating to the feeling on application and the makeup outcome of the two products for evaluation and comparison. The physical process of application was also specified.

The sensorial analysis room was controlled in terms of temperature and hygrometry, and was equipped with individual evaluation booths.

Each member of the panel evaluated the lipstick of the invention and the market lipstick by rating for eight sensorial descriptors, which were predefined and were the same across the whole panel, and which related to the lubricity, coverage, gloss, and comfort. They awarded a rating on a scale from 0 (highly mediocre) to 10 (excellent) for each of the descriptors, and only the significant means (alpha less than or equal to 5%) were retained in order to analyze the results.

The products were given 3-digit codes to allow blind testing.

Results:

At the time of application of the lipstick of the invention to the lips, the sensation is more lubricious than that of the prior-art lipstick without water and containing waxes. The sensation is more lubricious at the start (7.9/10 versus 2.8/10) and during the various passes (8.3/10 versus 3.7/10).

The lipstick is also consistently rated less sticky (4.4/10 versus 8.2/10 for the comparative product).

The lipstick is therefore more lubricious in use, whether at the time of starting or during the application.

The lipstick of the invention leaves the lips more supple immediately after application (7.2/10 as against 5.1/10), but also during the day (7.6/10 as against 6.0/10). During the day, the comfort is perceived as being superior (7.8/10 as against 5.9/10). The film is glossier (3/10 versus 0/10) and less present (4.5/10 as against 5.5/10).

These improvements are gained without detriment either to the coverage or to the hold of a film of product of the invention on the lips. The coverage of the product of the invention is equal to that of the prior-art product, but contains no wax, which is highly surprising (coverage of 8.6/10 as against 8.9/10). The hold, although very slightly lower than that of the product containing waxes, remains highly satisfactory (7.5/10 for the invention and 8.5/10 for the comparative product). It is much greater than the average hold of wax-free lip makeup products.

The invention claimed is:

1. A cosmetic skin or lip care or makeup composition in the form of a water-in-oil emulsion comprising a fatty phase, a surfactant, and water, wherein said fatty phase comprises at least two amides selected from dibutyl lauroyl glutamide and dibutyl ethylhexanoyl glutamide and at least one alkyl vinyl (co)polymer, said at least two amides represent between 2% and 3% by mass of the mass of the composition, said at least one alkyl vinyl (co)polymer represents between 3% and 20% by mass of the mass of the composition and is selected from the group consisting of compounds bearing the international nomenclature of cosmetic ingredients (INCI) names acrylates/dimethicone methacrylate copolymer, acrylates/behenyl acrylate/dimethicone methacrylate copolymer, acrylates/stearyl acrylate/dimethicone methacrylate copolymer, vinylpyrrolidone (VP)/hexadecene copolymer, triacontanyl polyvinyl pyrrolidone (PVP), and a mixture of vinylpyrrolidone (VP)/eicosene copolymer and an acrylate/stearyl acrylate/dimethicone methacrylate copolymer, and said composition is free of wax or comprises wax in an amount of less than 5% by mass.

2. The composition as claimed in claim 1, wherein the fatty phase comprises at least one first hydrocarbon nonvolatile oil and at least one second nonvolatile oil comprising at least one ester function and/or at least one alcohol function and at least one hydrocarbon chain comprising 10 to 22 carbon atoms.

3. The composition as claimed in claim 2, wherein the ratio by mass between the first nonvolatile oil and the second nonvolatile oil is between 1/3 and 3/1.

4. The composition as claimed in claim 2, wherein the composition comprises from 15 to 20% by mass of the first nonvolatile oil, from 8 to 15% by mass of the second nonvolatile oil, and from 8 to 12% by mass of a volatile oil.

5. The composition as claimed in claim 1, wherein the water represents from 10% to 35% by mass of the mass of the composition.

6. The composition as claimed in claim 1, wherein the composition is in the form of a stick.

7. A cosmetic method for skin or lip care or makeup, which comprises applying a composition as claimed in claim 1.

8. A method for manufacturing a composition as claimed in claim 1, the method comprising:
   the water and the surfactant are mixed and heated to give an aqueous phase,
   the fatty phase comprising the amide and the alkyl vinyl (co)polymer is melted,
   the aqueous phase is introduced into the melted fatty phase, to give a fluid mixture, and
   the fluid mixture is left to cool to ambient temperature, to give a composition in solid or creamy form.

9. The composition as claimed in claim 6, wherein the composition is in the form of a lipstick, a lip balm, a corrective stick, a foundation, a blusher or an eyeshadow.

* * * * *